United States Patent
Knauf et al.

(10) Patent No.: US 7,326,816 B2
(45) Date of Patent: Feb. 5, 2008

(54) PROCESS FOR THE PRODUCTION OF NITROBENZENE

(75) Inventors: Thomas Knauf, Dormagen (DE); Franz-Ulrich Von Gehlen, Krefeld (DE); Jörg Schmiedler, Shanghai (CN); Klaus Pilarczyk, Krefeld (DE); Peter Drinda, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/699,888

(22) Filed: Jan. 30, 2007

(65) Prior Publication Data

US 2007/0249873 A1    Oct. 25, 2007

(30) Foreign Application Priority Data

Feb. 3, 2006   (DE) .................. 10 2006 004 943

(51) Int. Cl.
*C07C 205/00* (2006.01)
*B01D 57/02* (2006.01)

(52) U.S. Cl. .................... 568/939; 204/450
(58) Field of Classification Search ............ 568/939; 204/450
See application file for complete search history.

(56) References Cited

U.S. PATENT DOCUMENTS

| 3,350,466 A | 10/1967 | Menke | 260/645 |
| 4,190,510 A | 2/1980 | Larbig | 204/180 R |
| 5,313,009 A | 5/1994 | Guenkel et al. | 568/927 |

FOREIGN PATENT DOCUMENTS

EP    1 132 347 A2    9/2001

*Primary Examiner*—J. Parsa
(74) *Attorney, Agent, or Firm*—Lyndanne M. Whalen

(57) ABSTRACT

Nitrobenzene is produced and then purified using an acidic wash, an alkaline wash, a neutral wash, subjecting a dispersion formed in the neutral wash to electrophoresis to separate water and benzene from the nitrobenzene and recover purified nitrobenzene.

2 Claims, No Drawings

PROCESS FOR THE PRODUCTION OF NITROBENZENE

BACKGROUND OF THE INVENTION

The present invention relates to a continuous process for the work-up of crude nitrobenzene. In this process, the crude nitrobenzene is washed in an acidic, in an alkaline and in a neutral wash consecutively. In the neutral wash, the organic phase containing nitrobenzene is first dispersed, then broken down in an electrophoresis unit and then the aqueous and organic phases are separated.

The prior art for neutral washing of crude nitrobenzene is dispersion of the organic phase with washing water using a mixing vessel or static mixer. The subsequent separation of the phases is conducted in separator vessels (settlers with or without coalescers) with the possible aid of demulsifiers (separating aids).

The basic electrophoresis process is described in DE-A-2 808 225. In this known process, an emulsion of nitrobenzene dispersed in waste sulfuric acid is produced in a batch process by stirring or recirculating, and this emulsion is then broken down in an electrode chamber.

DE-A-2808225 describes the workup of nitrobenzene from which excess benzene has already been separated. However, DE-A-2 808 225 does not disclose that the crude nitrobenzene contaminated with benzene has to be subjected to an acidic and then an alkaline wash followed by a neutral wash before the electrophoretic breaking down of the dispersion. Nor does this disclosure teach a separation of water and benzene to obtain higher purity of the nitrobenzene produced after the electrophoretic breaking down of the dispersion. Moreover, the process disclosed in DE-A-2 808 225 cannot be directly transferred to the purification of crude nitrobenzene by a neutral wash following the acidic and alkaline washes because, in the stages preceding the neutral wash, essential components affecting the result of the electrophoresis, such as sulfuric acid, are already washed out of the crude nitrobenzene.

SUMMARY OF THE INVENTION

The object of the present invention is therefore to provide a simple and economical process for the production of nitrobenzene in which nitrobenzene can be obtained in high purity without the addition of demulsifiers (separating aids) and with the smallest possible amounts of washing water.

This object is achieved by the process of the present invention in which crude nitrobenzene is treated with an acid wash, a basic wash and a neutral wash before forming the dispersion to be subjected to electrophoresis.

DETAILED DESCRIPTION OF THE INVENTION

The present invention relates to a process for the production of nitrobenzene, in which
a) benzene is reacted with nitrating acid to form crude nitrobenzene, and then
b) the crude nitrobenzene is washed with water in an acidic wash, and then
c) the crude nitrobenzene is washed with water in an alkaline wash, and then
d) the crude nitrobenzene is washed with water in a neutral wash, and then
e) water and benzene are removed from the crude nitrobenzene to obtain purified nitrobenzene.

In step d), the crude nitrobenzene is first mixed with water in a mixer and dispersed so that the organic phase containing nitrobenzene is present in at least partly dispersed form, and the dispersion is then fed into an electrophoresis unit in which the dispersion is broken down by applying direct-current electric voltage, and the aqueous and organic phases are then separated.

The nitration of benzene with nitrating acid (mixture of nitric acid and sulfuric acid) to form nitrobenzene in step a) generally takes place by a process from the prior art, e.g. according to EP-A-436 443. The nitration can take place with elimination of heat of reaction, e.g. isothermally, or adiabatically.

The crude nitrobenzene produced in step a) is generally first separated from excess sulfuric acid in a separator vessel. The crude nitrobenzene, which generally still contains traces of sulfuric acid, is then washed in an acidic wash in step b) and then separated from the acidic wash water, preferably by phase separation. The acidic wash water used preferably has a pH of $\leq 5$ (measured at 20° C.).

The crude nitrobenzene is then alkali-washed in an alkaline wash in step c) and then separated from the alkaline washing water, preferably by phase separation. The alkaline washing water used preferably has a pH of $\geq 9$ (measured at 20° C.). The subsequent workup of the alkaline waste water can take place by any of the known processes, e.g., according to EP-A-1 593 654.

The crude nitrobenzene thus obtained preferably has a temperature of 20°-60° C., most preferably of from 30°-50° C. The crude nitrobenzene thus obtained preferably contains from 4 to 10 wt. % benzene, based on the weight of the crude nitrobenzene, and less than 100 ppm, most preferably less than 60 ppm, nitrophenols, based on the weight of the crude nitrobenzene.

In step d), the crude nitrobenzene is washed in a neutral wash. In this step, the crude nitrobenzene is first mixed with water and dispersed so that the organic phase substantially containing nitrobenzene is present in at least partly dispersed form. The dispersion preferably contains from 5 to 20 wt. % water, based on the weight of the dispersion. This preferably takes place with a stirrer or a mixer or in a pump, most preferably in a centrifugal pump, the impeller of which runs at a minimum of 1450 rpm and preferably at least 2900 rpm. The energy input by the mixer is preferably 20 to 30 kW per $m^3$. Water droplets are produced with an area-average particle size of preferably less than 2,500 $\mu m^2$, more preferably less than 100 $\mu m^2$ and most preferably less than 10 $\mu m^2$.

In step d), deionized water (DI water) is preferably used as washing water, more preferably a mixture of DI water and condensate and most preferably steam condensate.

Following the mixing and dispersing, the dispersion is fed into an electrophoresis unit, in which the dispersion passes through a direct current field. During this process, the dispersion is broken down, i.e. the phase boundary is lowered and the phases separate again. In the electrophoresis unit, the dispersion passes through a direct current field of preferably 100 to 500 volts, more preferably 200 to 400 volts and most preferably 220 to 300 volts. The current strength is preferably from 0.05 to 3 amps and most preferably from 0.1 to 1 amp. The continuous operation of the washing process ensures that the electrode chamber of the electrophoresis unit is constantly flooded, so there is no risk of ignition of any flammable gas mixtures in the electrode chamber, even in the event of possible electrical arcing between the electrodes.

The organic and aqueous phases are then separated, preferably in a separator vessel.

The speed of the pumps for the production of the dispersion, the quantity of washing water used and the number of washing steps for the neutral wash (comprising pump, electrophoresis unit and separator vessel) determine the degree of purity that can be achieved for the nitrobenzene in step d).

In step e), the crude nitrobenzene is freed from water and benzene. This preferably takes place by distillation, with water and benzene and any light components being stripped overhead. The dried nitrobenzene remains, which has been freed from benzene and may still contain a small amount of dinitrobenzene, has a conductivity of preferably <50 µS/cm, more preferably <25 µS/cm, and most preferably a conductivity of <10 µS/cm.

The process according to the invention has the following advantages:

Low water consumption and, associated with this, a small quantity of waste water, high purity of the nitrobenzene end product, low investment costs through saving one to two washing steps depending on the degree of purity desired, avoidance of the use of chemical auxiliary substances such as demulsifiers, availability and reliability of the process.

Having thus described the invention, the following examples are given as being illustrative thereof.

EXAMPLES

Example 1

Comparative Example

Crude nitrobenzene from an isothermal nitrobenzene process was first subjected to an acidic wash and then alkalinized in a mixing vessel with the addition of sodium hydroxide solution (50%). In a downstream separator vessel, the mixture was then separated, due to the differences in density, into an organic phase (crude nitrobenzene) and an aqueous phase (waste lye). The aqueous phase was fed to a separate alkaline workup. The remaining warm crude nitrobenzene, at 31° C., contained 95 ppm dinitrobenzenes, 42 ppm nitrophenols and 100 ppm Monopol brilliant oil and had a benzene content of 4.8 wt. %. This warm crude nitrobenzene was neutral-washed in a four-step counter-current wash with a mixture of DI water and steam condensate. For this purpose, 4 mixing vessels with downstream separating apparatus (mixer/settler technology) were used. The crude nitrobenzene washed in this way was finally fed from the last separator vessel to a distillation column for drying and for separation of benzene and light components. The end product contained 30 ppm residual moisture, 99 ppm dinitrobenzenes, 2 ppm nitrophenols, <10 ppm benzene and had a conductivity of 20 µS/cm.

Example 2

Comparative Example

The crude nitrobenzene from an adiabatic nitrobenzene process was first fed into an acidic wash and then alkalinized in a mixing vessel with the addition of sodium hydroxide solution (50%). In a downstream separator vessel, the mixture was then separated, due to the differences in density, into an organic phase (crude nitrobenzene) and an aqueous phase (waste lye). The aqueous phase was fed to a separate alkaline workup. The remaining warm crude nitrobenzene, at 40° C., which contained 245 ppm dinitrobenzenes and 53 ppm nitrophenols and had a benzene content of 7.5 wt. %, was neutral-washed in a four-step counter-current wash. For this purpose, 4 mixing vessels (only the first 3 of which were stirred) with downstream separating apparatus (mixer/settler technology) were used. From the second washing step, Monopol brilliant oil was additionally used as a separating aid (the amount used being 10 ppm Monopol brilliant oil based on nitrobenzene). The crude nitrobenzene washed in this way was finally fed from the last separator vessel to a distillation column for drying and for the separation of benzene and light components. The end product contained 30 ppm residual moisture, 252 ppm dinitrobenzenes, 3 ppm nitrophenols, <10 ppm benzene and had a conductivity of 10 µS/cm.

Example 3

Example According to the Invention

The crude nitrobenzene from an adiabatic nitrobenzene process was first fed into an acidic wash and then alkalinized in a static mixer with the addition of sodium hydroxide solution (32%). In a downstream separator vessel, the mixture was then separated, due to the differences in density, into an organic phase (crude nitrobenzene) and an aqueous phase (waste lye). The warm crude nitrobenzene, at 39° C., which contained 179 ppm dinitrobenzenes and 51 ppm nitrophenols and had a benzene content of 6.8 wt. %, was combined in a first neutral wash with washing water from the second neutral wash on the inlet side of a centrifugal pump, which was operated at 2900 rpm. In this centrifugal pump, the first neutral wash of the crude nitrobenzene took place. The resulting dispersion was broken down using an electrophoresis unit operated at a direct current voltage of 280 V at 0.3 A and fed to a downstream separator vessel. The crude nitrobenzene from this separator vessel was then combined in the second neutral wash with washing water from the third neutral wash on the inlet side of a centrifugal pump, which was operated at 2900 rpm. In this centrifugal pump, the second neutral wash of the crude nitrobenzene took place. The resulting dispersion was broken down using a second electrophoresis unit operated at a direct current voltage of 240 V at 0.4 A and fed to a downstream separator vessel. The crude nitrobenzene from this separator vessel was then combined in the third neutral wash with washing water consisting of a mixture of DI water and steam condensate on the inlet side of a centrifugal pump, which was operated at 2900 rpm. In this centrifugal pump, the third neutral washing of the crude nitrobenzene took place. The resulting dispersion was broken down using a third electrophoresis unit operated at a direct current voltage of 290 V and 0.9 A and fed to a downstream separator vessel. The crude nitrobenzene washed in this way was finally fed from the last separator vessel to a distillation for drying and for the separation of benzene and light components. The nitrobenzene thus obtained contained 41 ppm residual moisture, 192 ppm dinitrobenzenes, 3 ppm nitrophenols, <2 ppm benzene and had a conductivity of 6 µS/cm.

Example 4

Example According to the Invention

The crude nitrobenzene from an adiabatic nitrobenzene process was first fed into an acidic wash and then alkalinized in a static mixer with the addition of sodium hydroxide solution (32%). In a downstream separator vessel, the mixture was then separated, due to the differences in density, into an organic phase (crude nitrobenzene) and an aqueous phase (waste lye). The warm crude nitrobenzene, at 41° C., which contained 184 ppm dinitrobenzenes and 55 ppm nitrophenols and had a benzene content of 6.3 wt. %, was combined in the first neutral wash with washing water from the second neutral wash on the inlet side of a centrifugal pump, which was operated at 2900 rpm. In this centrifugal pump, the first neutral wash of the crude nitrobenzene took place. The resulting dispersion was broken down using an electrophoresis unit operated at a direct current voltage of 280 V at 0.3 A and fed to a downstream separator vessel. The crude nitrobenzene from this separator vessel was then combined in the second neutral wash with washing water consisting of a mixture of DI water and steam condensate on the inlet side of a centrifugal pump, which was operated at 2900 rpm. In this centrifugal pump, the second neutral wash of the crude nitrobenzene took place. The resulting dispersion was broken down using a second electrophoresis unit operated at a direct current voltage of 280 V and 0.6 A and fed to a downstream separator vessel. The crude nitrobenzene washed in this way was finally fed from the last separator vessel to a distillation column for drying and for the separation of benzene and light components. The end product contained 45 ppm residual moisture, 196 ppm dinitrobenzenes, 6 ppm nitrophenols, <2 ppm benzene and had a conductivity of 23 µS/cm.

The essential data and results of the examples are compiled again in the following table. The table also reports how much washing water was used per ton of nitrobenzene (NB) in the neutral wash in step d).

The conductivity of the crude nitrobenzene before the neutral wash was >1000 µS/cm in all the examples.

ionic trace components contained in the end product, such as sodium sulfate, sodium nitrate or nitrophenols, with water and then measuring the electrical conductivity of the aqueous extract using a conductometer. The purity of nitrobenzene is given in µS/cm. The conductivity can be measured with a measuring instrument such as the type 702 conductometer from Knick. Method: a 500 ml nitrobenzene sample is extracted with 25 ml of demineralized water. The aqueous phase is then separated from the organic phase. The conductivity of the aqueous phase is finally determined with a conductometer.

A low conductivity indicates a high purity of the nitrobenzene sample.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of nitrobenzene comprising
   a) reacting benzene with nitrating acid to form nitrobenzene,
   b) washing the nitrobenzene formed in a) with water in an acidic wash,
   c) washing the nitrobenzene from b) with water in an alkaline wash,
   d) washing the nitrobenzene from c) with water in a neutral wash, and
   e) removing water and benzene from the nitrobenzene washed in d) to obtain purified nitrobenzene,
   in which
   step d) comprises:
   (i) mixing the nitrobenzene from c) with water in a mixer to at least partially disperse an organic phase substantially containing nitrobenzene in the water and form a dispersion, and
   (ii) feeding the dispersion into an electrophoresis unit in which the dispersion is broken down by applying a direct-current electric voltage.

2. The process of claim 1 in which d)(i) and d)(ii) are repeated using washing water from a subsequent washing step as water for a preceding washing step, and fresh water is used in the final step.

| Example | Process | Number of washing steps | Washing water (m³/t NB) | Number of electrophoreses | Brilliant oil yes/no | End product conductivity |
|---|---|---|---|---|---|---|
| 1 | Stirrer/settler | 4 | 0.23 | 0 | Yes | 20 µS/cm |
| 2 | Stirrer/settler | 4 | 0.3 | 0 | Yes | 10 µS/cm |
| 3 | Pump/settler | 3 | 0.16 | 3 | No | 6 µS/cm |
| 4 | Pump/settler | 2 | 0.16 | 2 | No | 23 µS/cm |

The separating agent used in Examples 1 and 2 was a sodium salt of a sulfated castor oil with the trade name Monopol brilliant oil from Degussa Site Krefeld, Stockhausen GmbH.

Conductivity determination method: measurement of ionic trace components in nitrobenzene by determining the electrical conductivity of the aqueous extract (on the basis of DIN 53779 "Determination of the electric conductivity and the specific resistance (resistivity) of aqueous extracts"). The purity of nitrobenzene is determined by extracting the